(12) United States Patent
Kawakami et al.

(10) Patent No.: US 8,840,922 B2
(45) Date of Patent: Sep. 23, 2014

(54) TRANSDERMALLY ABSORBABLE DONEPEZIL-CONTAINING PREPARATION

(75) Inventors: Satoshi Kawakami, Higashikagawa (JP); Masahiro Yamaji, Higashikagawa (JP)

(73) Assignee: Teikoku Seiyaku Co., Ltd., Higashikagawa-shi (JP)

( * ) Notice: Subject to any disclaimer, the term of this patent is extended or adjusted under 35 U.S.C. 154(b) by 0 days.

(21) Appl. No.: 13/503,198

(22) PCT Filed: Oct. 18, 2010

(86) PCT No.: PCT/JP2010/068260
§ 371 (c)(1),
(2), (4) Date: Apr. 20, 2012

(87) PCT Pub. No.: WO2011/049038
PCT Pub. Date: Apr. 28, 2011

(65) Prior Publication Data
US 2012/0207816 A1    Aug. 16, 2012

(30) Foreign Application Priority Data
Oct. 21, 2009   (JP) .................. 2009-242656

(51) Int. Cl.
*A61K 9/70*      (2006.01)
*A61K 31/445*    (2006.01)
(52) U.S. Cl.
CPC ............. *A61K 31/445* (2013.01); *A61K 9/7053* (2013.01)
USPC .......................................... 424/449; 424/448
(58) Field of Classification Search
CPC ..... A61K 9/00; A61K 9/0012; A61K 9/0014; A61K 9/70; A61K 9/7038; A61K 9/703
USPC .................................................. 424/448, 449
See application file for complete search history.

(56) References Cited

U.S. PATENT DOCUMENTS

| | | | |
|---|---|---|---|
| 5,834,010 A | 11/1998 | Quan et al. | |
| 2009/0175929 A1* | 7/2009 | Terahara et al. | 424/449 |
| 2010/0010043 A1 | 1/2010 | Hanatani et al. | |

FOREIGN PATENT DOCUMENTS

| | | |
|---|---|---|
| JP | 11-315016 A | 11/1999 |
| JP | 2001-39865 A | 2/2001 |
| JP | 2007-302582 A | 11/2007 |
| JP | 2009-22730 A | 2/2009 |
| WO | WO 03/032960 A1 | 4/2003 |
| WO | WO 2009/145269 A1 | 12/2009 |

OTHER PUBLICATIONS

International Search Report including English language translation dated Dec. 7, 2010 (Six (6) pages).

* cited by examiner

*Primary Examiner* — Michael G Hartley
*Assistant Examiner* — Micah-Paul Young
(74) *Attorney, Agent, or Firm* — Crowell & Moring LLP

(57) ABSTRACT

Provided is a donepezil-containing transdermal absorption formulation that can sustainably administer donepezil for a long period of time, and can provide both a rapid increase in the blood level of donepezil and donepezil sustained release properties. The donepezil-containing transdermal absorption formulation is a transdermal absorption formulation produced by dissolving donepezil, which is the active ingredient, in an adhesive patch base that contains a hydrophobic polymer and an absorption promoter. The absorption promoter is one kind or two or more kinds selected from lauryl alcohol, triethyl citrate, isopropyl myristate, cetyl lactate, oleyl alcohol, sorbitan monooleate, polyethylene glycol monostearate, lauromacrogol, N-methyl-2-pyrrolidone, and triacetin.

9 Claims, 2 Drawing Sheets

TRANSDERMALLY ABSORBABLE DONEPEZIL-CONTAINING PREPARATION

TECHNICAL FIELD

The present invention relates to a transdermal absorption formulation that includes a supporting material and an adhesive layer containing an adhesive base and a drug. More specifically, the present invention relates to an antidementia medication transdermal absorption formulation in which the drug contained as the active ingredient is donepezil to be used for dementia treatment.

BACKGROUND ART

Donepezil is a drug having an acetylcholinesterase inhibitory action that is widely used as a medication for suppressing the progression of the symptoms of dementia in Alzheimer-type dementia, or so-called Alzheimer's disease. In Alzheimer's disease, for which impairment of the cholinergic system in the brain has been reported, an acetylcholinesterase inhibitor like donepezil increases the amount of acetylcholine in the brain, and stimulates the cholinergic system in the brain. Conventionally, examples of actually used donepezil formulations have included oral administrations, such as tablets, capsules, syrups, and granules, as well as injections and rectal administration.

However, for patients with advanced symptoms of dementia, it is often difficult for the patient to take an antidementia drug. As a dosage form that is suited to such a case, Patent Document 1 describes a transdermal formulation and a suppository that contain donepezil. However, Patent Document 1 is an invention that mainly relates to an ointment, cream, or suppository, which does not sustainably administer an active ingredient over a long period of time.

Further, in Patent Document 2, a plaster agent containing donepezil is described, which has a skin permeation rate of at least 1.2 $\mu g/cm^2/hr$ or higher. However, since the active ingredient is dispersed in an adhesive patch, the drug transdermal absorption properties, in particular, a rapid increase in the level of the drug in the blood after administration, are insufficient.

PRIOR ART LIST

Patent Document

Patent Document 1: Japanese Patent Application Laid-Open Hei. 11-315016
Patent Document 2: International Patent Publication WO 03/032960

DISCLOSURE OF INVENTION

Problem to be Solved by the Invention

Therefore, to solve the conventional problems, it is an object of the present invention to provide a donepezil-containing transdermal absorption formulation that can sustainably administer donepezil over a long period of time, and can realize both a rapid increase in the level of donepezil in the blood, and donepezil sustained release properties.

Further, it is another object of the present invention to provide, in a transdermal absorption formulation including an absorption promoter, a highly stable transdermal absorption formulation that prevents crystallization of a main drug that is caused by containing of the transdermal absorption promoter, so that the donepezil does not crystallize even under long term storage conditions.

Means for Solving the Problem

To solve these problems, as a result of diligent research, the present inventors found that the skin permeation rate of a drug could be increased by using a transdermal absorption formulation in which donepezil, which is the active ingredient, is dissolved in an adhesive patch base that contains a hydrophobic polymer and an absorption promoter.

In addition, in particular, for a formulation (hereinafter sometimes referred to as "SIS formulation") that has a styrene-isoprene-styrene block copolymer (hereinafter sometimes referred to as "SIS") as a main base, the present inventors also found that a formulation that has high transdermal absorption properties of a main drug and is capable of stably releasing the main drug without crystallization of donepezil even under long term storage conditions could be provided by blending a hydrogenated rosin glycerin ester acting as a tackifier and donepezil as the main drug ingredient in an optimum blend ratio.

Moreover, the present inventors also found that in the SIS formulation, crystallization of the donepezil in the formulation could be prevented without reducing the adhesion properties of the formulation by optimizing the blend ratio between the SIS and liquid paraffin, thereby completing the present invention.

Therefore, the present invention is a transdermal absorption formulation having the following specific composition. Specifically, the basic aspects of the present invention are as follows.

(1) A transdermal absorption formulation produced by dissolving donepezil, which is an active ingredient, in an adhesive patch base that contains a hydrophobic polymer and an absorption promoter.

(2) The transdermal absorption formulation according to the above (1), wherein the absorption promoter is one kind or two or more kinds selected from lauryl alcohol, triethyl citrate, isopropyl myristate, cetyl lactate, oleyl alcohol, sorbitan monooleate, polyethylene glycol monostearate, lauromacrogol, N-methyl-2-pyrrolidone, and triacetin.

(3) The transdermal absorption formulation according to the above (1) or (2), wherein the absorption promoter is one kind or two or more kinds selected from lauryl alcohol, isopropyl myristate, lauromacrogol, and triacetin.

Among these, one aspect of the present invention is an SIS formulation, specifically, includes the following ones.

(4) A transdermal absorption formulation produced by dissolving donepezil, which is an active ingredient, in an adhesive patch base that contains a styrene-isoprene-styrene block copolymer, a hydrogenated rosin glycerin ester, liquid paraffin, and an absorption promoter.

(5) The transdermal absorption formulation according to the above (4), wherein the absorption promoter is one kind or two or more kinds selected from lauryl alcohol, lauromacrogol, and triacetin.

(6) The transdermal absorption formulation according to the above (4) or (5), wherein a blended amount of the absorption promoter is 1 to 10 wt %.

(7) The transdermal absorption formulation according to any of the above (4) to (6), wherein a blend ratio between the hydrogenated rosin glycerin ester and donepezil is hydrogenated rosin glycerin ester/donepezil=1.5 to 8.

(8) The transdermal absorption formulation according to any of the above (4) to (7), wherein a blend ratio between the styrene-isoprene-styrene block copolymer and liquid paraffin is styrene-isoprene-styrene block copolymer/liquid paraffin=0.7 to 1.5.

Therefore, most specifically, the present invention is as follows.

(9) A transdermal absorption formulation produced by dissolving 5 to 30 wt % of donepezil, which is an active ingredient, in an adhesive patch base that contains 5 to 90 wt % of a styrene-isoprene-styrene block copolymer, 5 to 70 wt % of a hydrogenated rosin glycerin ester, and 10 to 70 wt % of liquid paraffin, wherein a blend ratio between the hydrogenated rosin glycerin ester and donepezil is hydrogenated rosin glycerin ester/donepezil=1.5 to 8, and a blend ratio between the styrene-isoprene-styrene block copolymer and liquid paraffin is styrene-isoprene-styrene block copolymer/liquid paraffin=0.7 to 1.5.

Further, as another aspect, the present invention is the following.

(10) A transdermal absorption formulation produced by dissolving donepezil, which is an active ingredient, in an adhesive patch base that contains an acrylic polymer and, as an absorption promoter, isopropyl myristate.

(11) The transdermal absorption formulation according to the above (10), wherein a blended amount of the isopropyl myristate as an absorption promoter is 10 to 30 wt %.

Effect of the Invention

According to the present invention, a dissolved-type donepezil-containing transdermal absorption formulation is provided that contains a hydrophobic polymer and an absorption promoter.

By using the dissolved-type donepezil-containing transdermal absorption formulation provided by the present invention, the advantageous effects of a rapid increase in the level of donepezil in the blood after administration and exhibition of an effective blood level over a long period of time can be realized.

Further, the present invention can provide a formulation that exhibits stable main drug release properties without the occurrence of crystallization of the main drug even during long term storage.

Therefore, according to the donepezil-containing transdermal absorption formulation provided by the present invention, donepezil can be efficiently absorbed into the blood circulation via the skin. Thus, the transdermal absorption formulation has the advantageous effect that side effects on the digestive system that are seen in oral administration and side effects on the nervous system that can be caused by a sudden increase in the blood level can be avoided.

Consequently, even for patients with advanced symptoms of dementia, the present invention can provide a donepezil-containing transdermal absorption formulation that can sustainably administer donepezil efficiently, and that is very effective in the treatment of patients with advanced dementia.

MODES FOR CARRYING OUT THE INVENTION

Figure 1:
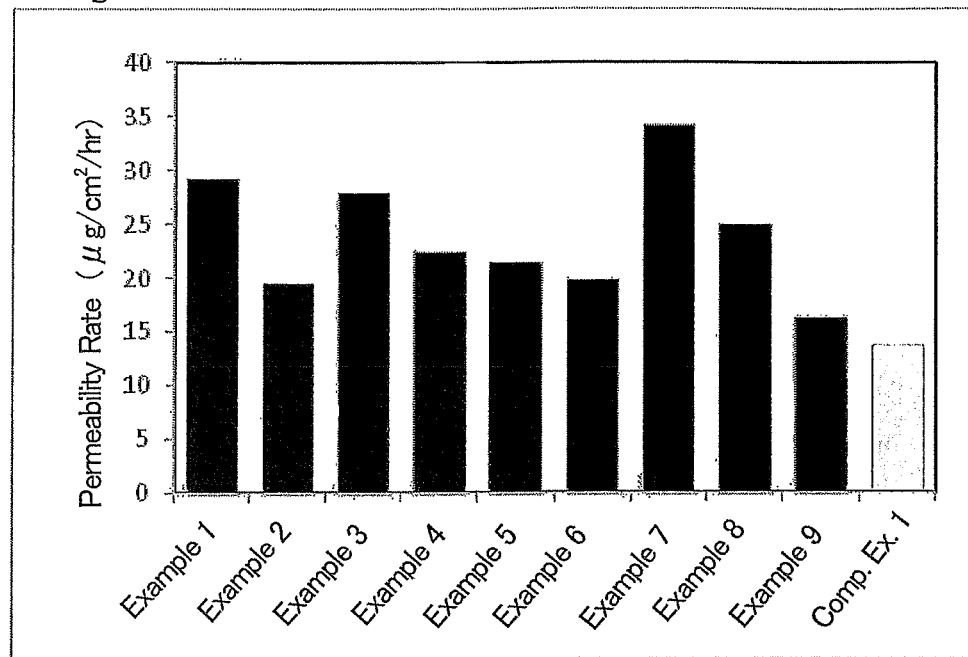
FIG. 1 is a graph illustrating the results of the in vitro skin permeation test of Test Example 1 of the present invention.

The donepezil-containing transdermal absorption formulation provided by the present invention will now be described in more detail.

The term "transdermal absorption formulation" in the present invention refers to an adhesive patch that includes at least a supporting material and an adhesive composition. This term includes reservoir type patches for external use having a drug storage layer, and single layer matrix type patches for external use.

Since matrix type patches for external use directly stick to the skin by the adhesive composition having the patch's self-adhesive force and containing the active ingredient, compared with reservoir type patches for external use, matrix type patches have superior adhesion properties as well as better drug absorption properties.

Therefore, although the transdermal absorption formulation of the present invention will mainly be described on the basis of a matrix type patch as an example, the present invention is not limited to this.

The form of the transdermal absorption formulation provided by the present invention is not particularly limited, as long as the adhesive composition includes donepezil dissolved therein, and the donepezil is released at a pharmacologically effective rate.

Typically, a transdermal absorption formulation is formed from an adhesive layer containing the drug (donepezil) and a supporting material laminated on the rear face of the adhesive layer. It is preferred that this adhesive layer has a self-adhesive force that can stick over an effective surface area sufficient for treatment on the surface of the skin for 24 hours or more. However, if this is difficult, a sheet-like cover that has a greater surface area than the drug-containing layer and has an adhesive force can also be used.

The transdermal absorption formulation of the present invention can supply a drug stably without any adherence problems by dissolving donepezil and/or a pharmaceutically acceptable salt thereof in the adhesive composition.

Examples of the type of salt may include, but are not particularly limited to, hydrochlorides, sulfates, mesylates, citrates, fumarates, tartrates, maleates, and acetates.

Therefore, in the present invention, the term donepezil refers to both donepezil and a pharmaceutically acceptable salt thereof.

Further, the blended amount of the donepezil is, based on the weight of the total adhesive composition, 5 to 30 wt %, preferably 5 to 20 wt %, and more preferably 10 to 20 wt %.

The adhesive composition of the present invention contains a hydrophobic polymer as the adhesive composition having a self-adhesive force.

Although the hydrophobic polymer is not particularly limited, it is preferred to use a rubber polymer, an acrylic polymer, or a silicon polymer.

Examples of the rubber polymer include a styrene-isoprene-styrene block copolymer, isoprene, polyisobutylene (hereinafter, "PIB"), a styrene-butadiene-styrene block copolymer (hereinafter, "SBS"), and a styrene-butadiene rubber (hereinafter, "SBR"). Among these, SIS is preferred.

The acrylic polymer is not particularly limited, as long as it has been copolymerized to include at least one kind of (meth) acrylic derivative represented by 2-ethylhexyl acrylate, methyl acrylate, butyl acrylate, hydroxyethyl acrylate, 2-ethylhexyl methacrylate and the like.

Specific examples include adhesives listed in "Iyakuhin Tenkabutsu Jiten 2007" (Dictionary of Drug Excipients 2007, Ed. by the Japan Pharmaceutical Excipients Council), such as an acrylic acid/octyl acrylate copolymer, 2-ethylhexyl acrylate/vinylpyrrolidone copolymer solution, acrylate/vinyl acetate copolymer, 2-ethylhexyl acrylate-2-ethylhexyl methacrylate/dodecyl methacrylate copolymer, copolymer resin emulsion of methyl acrylate/2-ethylhexyl acrylate, and acrylic polymers in acrylic resin alkanolamine solutions, as well as the DURO-TAK Acrylic Adhesive Series (manufactured by Henkel Corp.), Eudragit Series (manufactured by Higuchi, Inc.) and the like.

Specific examples of the silicon polymer include silicone rubbers, such as polyorganosiloxane.

Two kinds or more of these hydrophobic polymers may be mixed together for use. The blended amount of these polymers is, in consideration of forming the adhesive layer and sufficient permeability, based on the weight of the total composition of these polymers, 5 to 90 wt %, preferably 10 to 80 wt %, and more preferably 10 to 70 wt %.

It is preferred that the adhesive composition in the transdermal absorption formulation provided by the present invention contains an absorption promoter. Examples of absorption promoters that can be used include a fatty acid ester, a higher alcohol, a surfactant and the like.

Specific examples of the absorption promoter include methyl laurate, hexyl laurate, triethyl citrate, isopropyl myristate (hereinafter, "IPM"), myristyl myristate, octyldodecyl myristate, cetyl palmitate, triacetin, cetyl lactate, lauryl lactate, methyl salicylate, glycol salicylate, ethylene glycol salicylate, diethyl sebacate, diisopropyl sebacate, medium-chain fatty acid triglyceride, lauryl alcohol, stearyl alcohol, isostearyl alcohol, myristyl alcohol, oleyl alcohol, cetyl alcohol, glycerin monocaprylate, glycerin monocaprate, glycerin monolaurate, glycerin monooleate, sorbitan monolaurate, sorbitan monooleate, sucrose monolaurate, polysorbate 20, propylene glycol monolaurate, polyethylene glycol monolaurate, polyethylene glycol monostearate, lauromacrogol, HCO-60, diethanolamide laurate, N-methyl-2-pyrrolidone, Crotamiton, and dimethyl sulfoxide. Preferred are triethyl citrate, isopropyl myristate, cetyl lactate, oleyl alcohol, sorbitan monooleate, polyethylene glycol monostearate, lauromacrogol, N-methyl-2-pyrrolidone, and triacetin.

Among these, a formulation in which one kind or two or more kinds selected from isopropyl myristate, lauromacrogol, lauryl alcohol, and triacetin can exhibit high main drug release properties when initially attached, and excellent drug sustained release properties. In particular, when SIS is used as the hydrophobic polymer, the effects when combined with lauromacrogol, lauryl alcohol, or triacetin are high. Further, when an acrylic polymer is used, it is preferred to use in combination with isopropyl myristate.

In consideration of sufficient permeability of the main drug as an adhesive patch formulation, as well as skin irritancy such as reddening and edema, it is preferred to blend about 0.01 to 30 wt % of such an absorption promoter based on the weight of the total adhesive layer composition. In particular, when using a combination of SIS and one kind or two or more kinds selected from triacetin, lauromacrogol, and lauryl alcohol, the blended amount of these absorption promoters is preferably 1 to 10 wt %, and more preferably 3 to 8 wt %. On the other hand, when using a combination of an acrylic polymer and isopropyl myristate, the blended amount of the absorption promoter is preferably 10 to 30 wt %, and more preferably 20 to 30 wt %. If the blended amount of the absorption promoter is less than 0.01%, the desired main drug release properties cannot be obtained, while if the blended amount is more than 30 wt %, undesirable effects, such as deterioration in the formulation properties or an increase in skin irritancy, occur.

The adhesive composition in the transdermal absorption formulation provided by the present invention may also contain a plasticizer. Examples of plasticizers that can be used include petroleum-based oils (for example, paraffinic process oil, naphthenic process oil, aromatic process oil and the like), squalane, squalene, vegetable oils (for example, olive oil, camellia oil, tall oil, peanut oil, castor oil and the like), silicone oil, dibasic acid esters (for example, dibutyl phthalate, dioctyl phthalate and the like), liquid rubber (for example, polybutene, liquid isoprene rubber and the like), a liquid fatty acid ester (isopropyl myristate, hexyl laurate, diethyl sebacate, diisopropyl sebacate and the like), diethylene glycol, polyethylene glycol, propylene glycol, dipropylene glycol and the like. Particularly preferred is liquid paraffin, liquid polybutene, or silicone oil. Most preferred is liquid paraffin.

Two kinds or more of these components may be mixed together for use. The total blended amount of such plasticizers based on the total adhesive layer composition is, in consideration of sufficient skin permeability and a sufficient cohesive force as a patch formulation, 10 to 70 wt %, preferably 10 to 60 wt %, more preferably 10 to 50 wt %, and even more preferably 10 to 30 wt %.

It is preferred to blend a tackifier resin in the adhesive layer of the present invention in order to adjust the adhesive force of the formulation. Further, some tackifier resins exhibit an action for dissolving donepezil, so that such a tackifier resin may also be used to regulate the solubility of the donepezil in the adhesive.

Examples of tackifier resins that can be used include rosin derivatives (for example, rosin, rosin glycerin ester, hydrogenated rosin, hydrogenated rosin glycerin esters, rosin pentaerythritol ester and the like), alicyclic saturated hydrocarbon resins (for example, ARKON P100 manufactured by Arakawa Chemical Industries, Ltd.), aliphatic hydrocarbon resins (for example, QUINTONE B170 manufactured by Zeon Corporation), terpene resins (for example, CLEARON P-125 by Yasuhara Chemical Co., Ltd.), maleic acid resins and the like. From the perspectives of the adhesion properties of the formulation and the solubility of the donepezil in the formulation, a hydrogenated rosin glycerin ester is particularly preferred.

The blended amount of such a tackifier resin based on the total composition of the adhesive composition is, in consideration of sufficient adhesive force as an adhesive formulation and irritancy on the skin when peeling off, 5 to 70 wt %, preferably 5 to 60 wt %, and more preferably 10 to 50 wt %.

Since the donepezil-containing transdermal absorption formulation provided by the present invention is a systemic action transdermal absorption formulation, crystallization of the main drug during storage can lead to a decrease in the level of donepezil in the blood while the patch is adhered, which is not desirable. Therefore, it is preferred that donepezil crystals do not form in the formulation even under long-term storage conditions. However, because the present invention is a formulation that includes a transdermal absorption promoter, it is difficult to maintain the homogeneity of the base in a long-term storage product, so that crystallization of the main drug can occur due to the increasing heterogeneity of the base.

Thus, for an SIS formulation, attempts have been made to increase the solubility of the donepezil by making a hydrogenated rosin glycerin ester function as a donepezil solubilizer in addition to functioning as a tackifier resin. However, when the hydrogenated rosin glycerin ester is added in a certain amount or more, deterioration in the main drug release properties is seen due to the solubility of the donepezil becoming too high. Therefore, it is essential to blend the hydrogenated rosin glycerin ester in an appropriate blend ratio.

Based on investigations carried out by the present inventors, it was found that a preferred blend ratio of the hydrogenated rosin glycerin ester and donepezil in the donepezil-containing transdermal absorption formulation of the present invention is hydrogenated rosin glycerin ester/donepezil=1.5 to 8, more preferably 1.5 to 5, and still more preferably 2 to 4. Specifically, if hydrogenated rosin glycerin ester/donepezil is less than 1.5, there is a risk of crystallization of the main drug in the formulation during storage due to the low solubility of the donepezil in the formulation, while if this ratio is more than 8, the main drug release properties deteriorate.

Further, it was also found that there is a relationship between the SIS blended amount and crystallization of donepezil in an SIS formulation. Specifically, by including SIS, the mobility of donepezil in the formulation is suppressed, which means that crystallization of the main drug can be suppressed. However, when a large amount of SIS is contained, this may also cause deterioration in the adhesion properties of the formulation.

Conversely, blending liquid paraffin promotes donepezil crystallization. Specifically, by blending liquid paraffin, not only is the mobility of donepezil in the formulation promoted, but since the liquid paraffin has a low solubility in donepezil, the donepezil solubility in the overall formulation is reduced. However, suppressing the blended amount of liquid paraffin leads to deterioration in the adhesion properties.

In view of this situation, the present invention enables crystallization of the donepezil to be suppressed without harming adhesion properties by optimizing the blend ratio between liquid paraffin and SIS.

Specifically, the blend ratio between SIS and liquid paraffin in the present invention is SIS/liquid paraffin=0.7 to 1.5, and preferably 0.8 to 1.5. If SIS/liquid paraffin is less than 0.7, the blended amount of liquid paraffin is excessive, so that donepezil crystallization during long-term storage can occur. On the other hand, if SIS/liquid paraffin is more than 1.5, since the SIS content is too high, this can cause deterioration in the adhesive force.

The transdermal absorption formulation provided by the present invention can optionally use an antioxidant, fillers, a crosslinking agent, a preservative, and a UV-absorber.

Preferred examples of the antioxidant include tocopherols and ester derivatives thereof, ascorbic acid, ascorbyl stearate, nordihydroguaiaretic acid, dibutylhydroxytoluene (hereinafter, "BHT"), butylhydroxyanisole and the like.

Preferred examples of the fillers include calcium carbonate, magnesium carbonate, silicates (for example, aluminum silicate, magnesium silicate and the like), silicic acid, barium sulfate, calcium sulfate, calcium zincate, zinc oxide, titanium oxide, silicon dioxide and the like.

Preferred examples of the crosslinking agent include thermosetting resins such as amino resins, phenolic resins, epoxy resins, alkyd resins, and unsaturated polyesters, organic crosslinking agents such as isocyanate compounds and block isocyanate compounds, and inorganic crosslinking agents such as metals or metal compounds.

Preferred examples of the preservative include ethyl paraoxybenzoate, propyl paraoxybenzoate, butyl paraoxybenzoate and the like.

Preferred examples of the UV absorber include p-aminobenzoic acid derivatives, anthranilic acid derivatives, salicylic acid derivatives, amino acid compounds, dioxane derivatives, coumarin derivatives, imidazoline derivatives, pyrimidine derivatives and the like.

The antioxidant, fillers, crosslinking agent, preservative, UV-absorber and the like can be blended in an amount of preferably 10 wt % or less, more preferably 5 wt % or less, and most preferably 2 wt % or less, based on the weight of the total composition of the adhesive layer in the formulation.

The transdermal absorption formulation of the present invention that has such a composition as described above may be produced by any method. Examples of the method include a method commonly referred to as a "hot-melt method", in which a drug-containing base composition is heated to dissolve, the dissolved base composition is coated on a release film or a supporting material, and then the resultant object is bonded to a supporting material or a release film; and a method commonly referred to as a "solvent method", in which the drug-containing base component is dissolved in a solvent such as toluene, hexane, and ethyl acetate, the resultant mixture is extended over a release film or a supporting material, the solvent is removed by drying, and then the resultant object is bonded to a supporting material or a release film.

The supporting material for the transdermal absorption formulation of the present invention may be elastic or non-elastic supporting material. For example, the supporting material can be selected from among non-woven fabric, polyurethane, polyester, polyvinyl acetate, polyvinylidene chloride, polyethylene, polyethylene terephthalate (hereinafter, "PET"), aluminum sheet and the like, and a composite material of these examples.

Further, the release film is not particularly limited, as long as the adhesive layer is protected and the contained antidementia medication donepezil does not alter until the transdermal absorption formulation is applied on the skin, and as long as the film is silicon-coated so that it can be easily peeled off.

Specific examples include silicon-coated polyethylene film, polyethylene terephthalate film, or polypropylene film.

The thus-prepared transdermal absorption formulation of the present invention is prepared by dissolving the active ingredient donepezil in an adhesive patch base in which a hydrophobic polymer, an absorption promoter, and the above described various additives are blended. With this formulation, the excellent effects of a rapid increase in the level of donepezil in the blood after administration and maintenance of an effective blood level for a long time are exhibited.

EXAMPLES

The present invention will now be described in more detail using the following Examples of the invention. However, the present invention is not limited to these Examples, and the present invention may be variously modified within the technical scope of the invention. Further, in the following Examples, unless otherwise stated, "%" means "wt %".

Example 1

(Formula)

| | |
|---|---|
| SIS | 15% |
| Liquid Paraffin | 24% |
| BHT | 1% |
| Hydrogenated Rosin Glycerin Ester | 35% |

-continued

| | |
|---|---|
| Triacetin | 5% |
| Donepezil | 20% |
| Total Amount | 100% |

First, the donepezil was dissolved in a mixed solution of triacetin and toluene. Then, the remaining components dissolved in toluene were added to the mixture. Next, the mixture was coated on a release film, and the toluene was then removed by drying. The coated release film was then bonded to a PET film support to obtain the transdermal absorption formulation of the present invention.

Examples 2 to 10

Using the blends shown in the following Table 1, the transdermal absorption formulations of Examples 2 to 10 of the present invention were obtained based on the method described in Example 1 as described above.

TABLE 1

| | Example | | | | | | | | | |
|---|---|---|---|---|---|---|---|---|---|---|
| Component | 1 | 2 | 3 | 4 | 5 | 6 | 7 | 8 | 9 | 10 |
| SIS | 15 | 16 | 15 | 17 | 15 | 15 | 15 | 16 | 17 | 17 |
| Liquid Paraffin | 24 | 23 | 24 | 23 | 24 | 24 | 24 | 23 | 23 | 21 |
| BHT | 1 | 1 | 1 | 1 | 1 | 1 | 1 | 1 | 1 | 1 |
| Hydrogenated Rosin Glycerin Ester | 35 | 35 | 35 | 34 | 35 | 35 | 35 | 35 | 34 | 34 |
| Triacetin | 5 | | | | | | | | | 5 |
| Triethyl citrate | | 5 | | | | | | | | |
| Isopropyl Myristate | | | 5 | | | | | | | |
| Cetyl Lactate | | | | 5 | | | | | | |
| Polyethylene Glycol Monolaurate | | | | | 5 | | | | | |
| Sorbitan Monoaleate | | | | | | 5 | | | | |
| Lauromacrogol | | | | | | | 5 | | | |
| Oleyl Alcohol | | | | | | | | 5 | | |
| N-methyl-2-pyrrolidone | | | | | | | | | 5 | 2 |
| Donepezil | 20 | 20 | 20 | 20 | 20 | 20 | 20 | 20 | 20 | 20 |
| Total | 100 | 100 | 100 | 100 | 100 | 100 | 100 | 100 | 100 | 100 |

Comparative Example 1

A transdermal absorption formulation as Comparative Example 1 was prepared in the same manner as Example 1, except that the absorption promoter (triacetin) was not added. Further, the production steps were the same as in Example 1.

Examples 11 to 21

Using the blends shown in the following Table 2, the transdermal absorption formulations of Examples 11 to 21 were obtained based on the method described in Example 1, except that the blended amount of donepezil, and the blended amounts of triacetin, lauromacrogol, and lauryl alcohol as the absorption promoter were changed.

TABLE 2

| | Example | | | | | | | | | | |
|---|---|---|---|---|---|---|---|---|---|---|---|
| Component | 11 | 12 | 13 | 14 | 15 | 16 | 17 | 18 | 19 | 20 | 21 |
| SIS | 22 | 22 | 17 | 17 | 22 | 22 | 22 | 22 | 22 | 22 | 22 |
| Liquid Paraffin | 17 | 22 | 17 | 19.5 | 17 | 22 | 16 | 21 | 27 | 17 | 21 |
| BHT | 1 | 1 | 1 | 1 | 1 | 1 | 1 | 1 | 1 | 1 | 1 |
| Hydrogenated Rosin Glycerin Ester | 40 | 40 | 40 | 40 | 40 | 40 | 40 | 40 | 40 | 40 | 40 |
| Triacetin | 5 | 5 | 5 | 7.5 | | | | | | | |
| Lauromacrogol | | | | | 5 | 5 | 5 | 1 | | | |
| Lauryl Alcohol | | | | | | | | | 5 | 5 | 1 |

TABLE 2-continued

| | Example | | | | | | | | | | |
|---|---|---|---|---|---|---|---|---|---|---|---|
| Component | 11 | 12 | 13 | 14 | 15 | 16 | 17 | 18 | 19 | 20 | 21 |
| Silicon Dioxide | | | | | | | 1 | | | | |
| Donepezil | 15 | 10 | 20 | 15 | 15 | 10 | 15 | 15 | 5 | 15 | 15 |
| Total | 100 | 100 | 100 | 100 | 100 | 100 | 100 | 100 | 100 | 100 | 100 |

Example 22

(Formula)

| | |
|---|---|
| Acrylic Adhesive (DURO-TAK 87-2287, manufactured by Henkel Corp.) | 70% |
| IPM | 10% |
| Donepezil | 20% |
| Total Amount | 100% |

The transdermal absorption formulation of Example 22 of the present invention was obtained based on the above-described formula using an acrylic adhesive.

Specifically, the donepezil, IPM, and acrylic adhesive were thoroughly admixed in a solvent (ethyl acetate). The resultant mixture was coated on a release film, and the ethyl acetate was then removed by drying. The coated release film was then bonded to a PET film support to obtain the transdermal absorption formulation of the present invention.

Examples 23 to 25

The transdermal absorption formulations of Examples 23 to 25 of the present invention were obtained in the same manner as in Example 22 based on the formulas shown in the following Table 3.

Example 26

(Formula)

| | |
|---|---|
| Silicone Rubber (BIO-PSA 4601, manufactured by Dow Corning Corp.) | 75% |
| Triacetin | 5% |
| Donepezil | 20% |
| Total Amount | 100% |

The donepezil, triacetin, and silicone rubber were thoroughly admixed in a solvent (ethyl acetate). The resultant mixture was coated on a release film, and the ethyl acetate was then removed by drying. The coated release film was then bonded to a PET film support to obtain the transdermal absorption formulation of Example 26 of the present invention.

Comparative Example 2

A transdermal absorption formulation as Comparative Example 2 was prepared in the same manner as Example 22, except that the absorption promoter (IPM) was not added.
The production steps were the same as in Example 22.

The formulas for Examples 22 to 26 and Comparative Example 2 are collectively shown in Table 3.

TABLE 3

| | Example | | | | | Comparative |
|---|---|---|---|---|---|---|
| Component | 22 | 23 | 24 | 25 | 26 | Example 2 |
| Acrylic Adhesive | 70 | 56 | 52 | 64 | | 80 |
| Silicone Rubber | | | | | 75 | |
| SIS | | | 5 | | | |
| IPM | 10 | 30 | 30 | 10 | | |
| Rauromacrogol | | | | 10 | | |
| Triacetin | | | | | 5 | |
| Donepezil | 20 | 14 | 13 | 16 | 20 | 20 |
| Total | 100 | 100 | 100 | 100 | 100 | 100 |

Test Example 1

Skin Permeability Test in Hairless Rats

To investigate the drug release properties of donepezil for an SIS formulation, particularly the donepezil release properties from immediately after administration to when the patch is initially attached, an in vitro skin permeability test was carried out on rats using the respective transdermal absorption formulations of Examples 1 to 9 and Comparative Example 1.
[Method]
Abdominal skin from a hairless rat was peeled away, and the dermis side was made to face the receptor layer side. The inner side was suffused with phosphate buffered saline, and 37° C. warm water was refluxed through a water jacket.
The respective test formulations were cut into a circular shape (1.54 cm$^2$) and stuck on the excised skin. The receptor solution was sampled over time, and the skin permeation rate (μg/cm$^2$/hr) in a constant state (8 to 10 hours after the test was started) was calculated by measuring the donepezil permeation amount based on high-performance liquid chromatography.
[Results]
The results are shown in FIG. 1.
Based on the results shown in FIG. 1, it was confirmed that the formulations of Examples 1 to 9 of the present invention exhibit more rapid drug release properties than the formulation of Comparative Example 1.

Test Example 2

Skin Permeability Test in Rats

To investigate the drug release properties of donepezil for an SIS formulation, particularly the donepezil release properties from immediately after administration to when the patch is initially attached, an in vitro skin permeability test was carried out on rats using the respective transdermal absorption formulations of Examples 11 to 13, 15 to 18, 20, and 21.

[Method]

Abdominal skin from a hairless rat was peeled away, and the dermis side was made to face the receptor layer side. The inner side was suffused with phosphate buffered saline, and 37° C. warm water was refluxed through a water jacket.

The respective test formulations were cut into a circular shape (1.54 cm$^2$) and stuck on the excised skin. The receptor solution was sampled over time, and the skin permeation rate (μg/cm$^2$/hr) in a constant state (12 to 24 hours after the test was started) was calculated by measuring the donepezil permeation amount based on high-performance liquid chromatography.

[Results]

Figure 2:
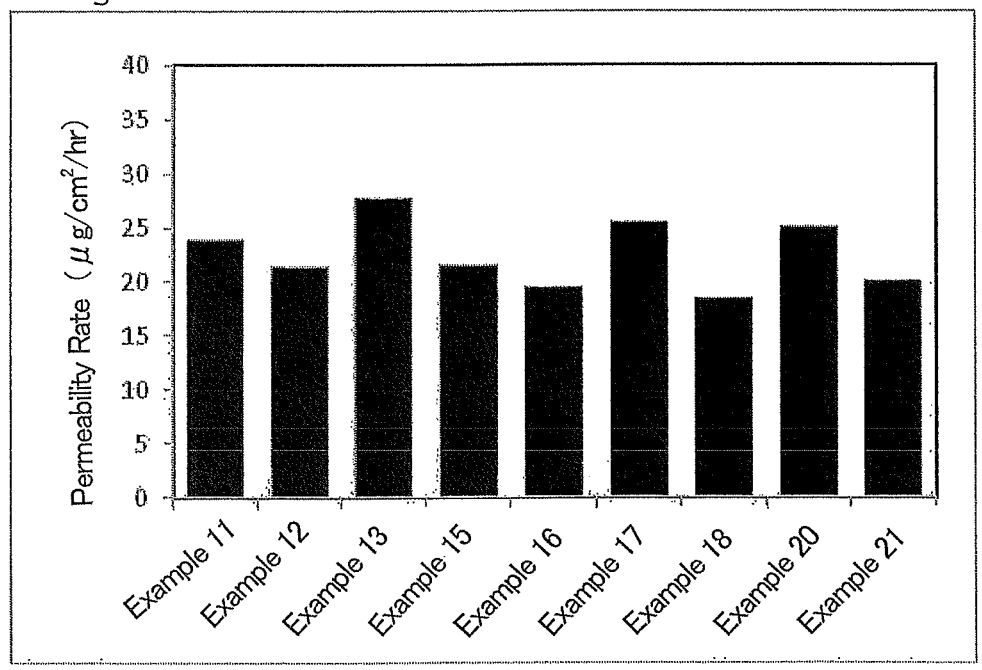
FIG. 2 is a graph illustrating the results of the in vitro skin permeation test of Test Example 2 of the present invention.

The results are shown in FIG. 2.

Based on the results shown in FIG. 2, it was confirmed that the formulations of the respective Examples exhibit rapid drug release properties. This point can be also confirmed by comparing the skin permeation rate with Comparative Example 1 of Test Example 1.

Test Example 3

Skin Permeability Test in Rats

To investigate the drug release properties of donepezil for an acrylic formulation, particularly, the donepezil release properties from immediately after administration to when the patch is initially attached, an in vitro skin permeability test was carried out on rats using the respective transdermal absorption formulations of Examples 23 to 25 and Comparative Example 2.

[Method]

Abdominal skin from a Wistar rat whose hair had been removed was peeled away, and the dermis side was made to face the receptor layer side. The inner side was suffused with phosphate buffered saline, and warm water (37° C.) was refluxed through a water jacket.

The respective test formulations were cut into a circular shape (1.54 cm$^2$) and stuck on the excised skin. The receptor solution was sampled over time, and the skin permeation rate (μg/cm$^2$/hr) in a constant state (12 to 24 hours after the test was started) was calculated by measuring the donepezil permeation amount based on high-performance liquid chromatography.

[Results]

Figure 3:
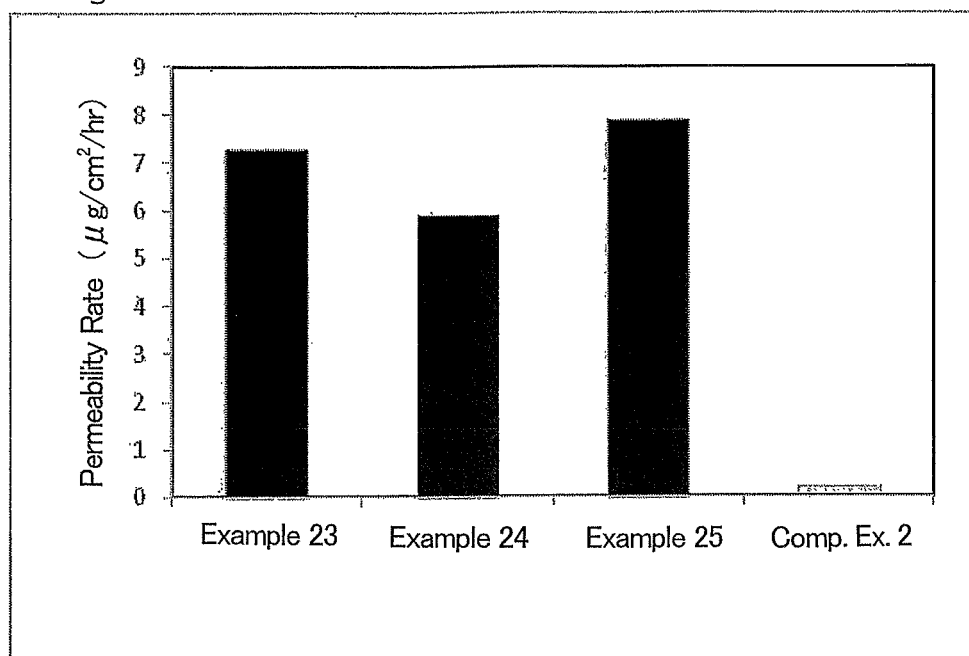
FIG. 3 is a graph illustrating the results of the in vitro skin permeation test of Test Example 3 of the present invention.
Figure 4:
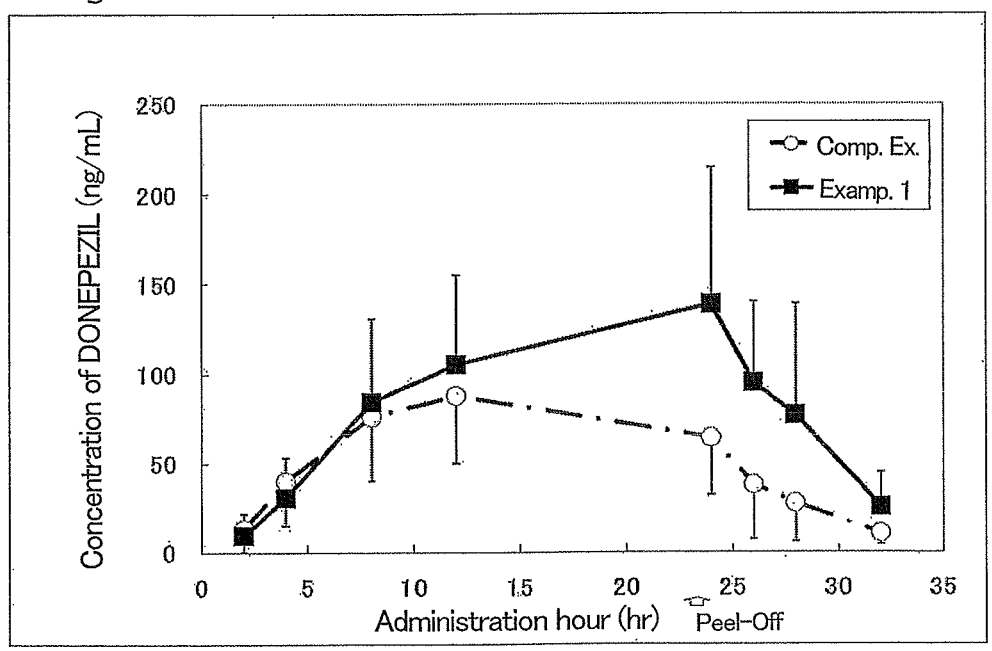
FIG. 4 is a graph illustrating the results of a test for measuring the level of donepezil in the blood of a rabbit for the donepezil-containing transdermal absorption formulation of the present invention.

The results are shown in FIG. 3.

It was confirmed that the formulations of the respective Examples of the present invention exhibit more rapid drug release properties than the formulation of Comparative Example 3.

Test Example 4

Rabbit Blood Level Measurement Test

A test for measuring the level of donepezil in the plasma of a rabbit was carried out using the transdermal absorption formulations of Example 1 and Comparative Example 1 (drug administration amount 70 mg, respectively).

Each of the adhesive patches (transdermal absorption formulations) was stuck on the back region of a rabbit where the hair had been removed, blood was collected over time, and the donepezil level in the plasma was measured based on LC-MS.

The results are shown in Table 4.

Based on the results, it was confirmed that the adhesive patch (transdermal absorption formulation) of Example 1 of the present invention can release a drug more sustainably than the adhesive patch (transdermal absorption formulation) of Comparative Example 1.

Test Example 5

Formulation Stability Test

The following stability test was carried out on a sample of each of the transdermal absorption formulations of Examples 1, 3, 7, 11, 17, 23, and 24, which had been stored for 1 month under storage conditions of 60° C. These results are shown in Table 4.

The test items were as follows.

(1) Observation of Presence or Absence of Crystal Precipitation on Formulation Surface Each of the stored formulations was observed as to the presence or absence of crystal precipitation on the surface of the formulation visually and with a microscope (×450).

Evaluation was performed as follows.

X: Crystal precipitation could be confirmed visually.

Δ: Crystal precipitation could be confirmed with a microscope.

◯: Crystal precipitation could not be confirmed.

(2) Main Drug Stability Test

The drug level in the formulations of Examples 11, 17, 23, and 24, in which crystal precipitation was not observed in the stored formulations, was measured by liquid chromatography, and the drug residual ratio (versus initial %) of each formulation after storage was calculated based on the donepezil content in each formulation prior to storage as an initial value (100%).

(3) Main Drug Release Stability Test

A release test on the formulations of Examples 11, 17, 23, and 24, in which crystal precipitation was not observed in the stored formulations, was carried out using a USP Drug Release Apparatus 6 (Cylinder) method to determine the release rate of donepezil by liquid chromatography.

TABLE 4

Results of Stability Test for Each Formulation

| | Example | | | | | | |
|---|---|---|---|---|---|---|---|
| | 1 | 3 | 7 | 11 | 17 | 23 | 24 |
| Crystal Precipitation | Δ | Δ | Δ | ◯ | ◯ | ◯ | ◯ |
| Main Drug Content (vs. initial %) | — | — | — | 98.4 | 100.2 | 97.3 | 99.9 |
| Release Properties (vs. initial %) | — | — | — | 100≧ | 92.3 | 100≧ | 100≧ |

In each of the stored formulations, there was no precipitation of crystals that could be visually confirmed. In particular, in Examples 11, 17, 23, and 24, respectively, crystal precipitation was not observed even under observation with a microscope.

Further, the main drug content, and release properties of the respective formulations of Examples 11, 17, 23, and 24 did not substantially deteriorate, and it was thus found that these were transdermal absorption formulations that exhibited excellent stability.

Test Example 6

Rabbit Skin Primary Irritancy Test

The skin primary irritancy of Examples 11, 13, 18 to 21, 23, and 24, and a commercially-available antidementia adhesive patch (Rivastigmine, 9.6 mg content) as a control agent, was tested based on the Draize method using a rabbit.

Each test formulation was adhered for 24 hours on healthy skin on the rabbit's back and on damaged skin. The skin condition was visually determined 1 hour, 24 hours, and 48 hours after peeling off the patch based on the determination criteria shown in Table 5, and a stimulation index of each of the test formulations was calculated.

The stimulation index determination criteria are shown in Table 5, and the measurement results are shown in Table 6.

TABLE 5

Determination Criteria

| Erythema & Crust Formation | Score | Edema Formation | Score |
| --- | --- | --- | --- |
| No Erythema | 0 | No Edema | 0 |
| Slight Erythema | 1 | Very Slight Edema | 1 |
| Clear Erythema | 2 | Slight Edema | 2 |
| Medium to Strong Erythema | 3 | Medium Edema | 3 |
| From Strong Erythema to Light Crust Formation | 4 | Strong Edema | 4 |

(1) The Stimulation Index was Determined Based on the Following Formula.

Stimulation index (SI)=[Sum Total Score of 1 and 48 hours after peeling off]/4

(2) The Irritancy Evaluation Based on the Obtained Stimulation index was performed as follows:

| Irritancy Evaluation | |
| --- | --- |
| SI = 0: | No irritancy |
| 0 < SI < 2: | Weak irritancy |
| 2 ≤ SI < 5: | Medium level irritancy |
| 5 ≤ SI: | Strong irritancy |

TABLE 6

| Test | Example | | | | | | | | Control |
| --- | --- | --- | --- | --- | --- | --- | --- | --- | --- |
| Formulation | 11 | 13 | 18 | 19 | 20 | 21 | 23 | 24 | Drug |
| stimulation Index (SI) | 2.9 | 3.0 | 3.0 | 3.0 | 3.0 | 2.8 | 2.5 | 2.5 | 3.3 |

Based on the above results, it could be confirmed that the transdermal absorption formulation of the present invention is a highly safe formulation that is as safe as or safer than a commercially available antidementia adhesive patch.

INDUSTRIAL APPLICABILITY

According to the donepezil-containing transdermal absorption formulation provided by the present invention, donepezil, which is the active ingredient, can be efficiently absorbed into the blood circulation via the skin.

Further, side effects on the digestive system that are seen in oral administration and side effects on the nervous system that can be caused by a sudden increase in blood level can be avoided. Moreover, the formulation is particularly effective as a formulation for external use that is intended for long term administration of donepezil, and can shed light on treatment of dementia.

The invention claimed is:

1. A transdermal absorption formulation produced by dissolving donepezil, which is an active ingredient, in an adhesive patch base containing a styrene-isoprene-styrene block copolymer, a hydrogenated rosin glycerin ester, liquid paraffin, and an absorption promoter, wherein
    (a) a blend ratio between the hydrogenated rosin glycerin ester and donepezil is hydrogenated rosin glycerin ester/donepezil=1.5 to 8, and
    (b) a blend ratio between the styrene-isoprene-stryene block copolymer and liquid paraffin is styrene-isoprene-styrene block copolymer/liquid paraffin=0.7 to 1.5.

2. The transdermal absorption formulation according to claim 1, wherein the absorption promoter is one kind or two or more kinds selected from lauryl alcohol, triethyl citrate, isopropyl myristate, cetyl lactate, oleyl alcohol, sorbitan monooleate, polyethylene glycol monostearate, lauromacrogol, N-methyl-2-pyrrolidone, and triacetin.

3. The transdermal absorption formulation according to claim 1 wherein the absorption promoter is one kind or two or more kinds selected from lauryl alcohol, isopropyl myristate, lauromacrogol, and triacetin.

4. The transdermal absorption formulation according to claim 1, wherein the absorption is one kind or two or more kinds selected from lauryl alcohol, lauromacrogol, and triacetin.

5. The transdermal absorption formulation according to claim 1, wherein a blended amount of the absorption promoter is 1 to 10 wt %.

6. A transdermal absorption formulation produced by dissolving 5 to 30 wt % of donepezil, which is an active ingredient, in an adhesive patch base containing 5 to 90 wt % of styrene-isoprene-styrene block copolymer, 5 to 70 wt % of a hydrogenated rosin glycerin ester, and 10 to 70 wt % of liquid paraffin, wherein a blend ratio between the hydrogenated rosin glycerin ester, and donepezil is hydrogenated rosin glycerin ester and donepezil is hydrogenated rosin glycerin ester/donepezil=1.5 to 8, and a blend ratio between the styrene-isoprene-styrene block copolymer and liquid paraffin is a styrene-isoprene-styrene block copolymer/liquid paraffin=0.7 to 1.5.

7. The transdermal absorption formulation according to claim 2 wherein the absorption promoter is one kind or two or more kinds selected from lauryl alcohol, isopropyl myristate, lauromacrogol, and triacetin.

8. The transdermal absorption formulation according to claim 4, wherein a blended amount of the absorption promoter is 1 to 10 wt %.

9. A transdermal absorption formulation produced by dissolving 5 to 30 wt % of donepezil, which is an active ingredient, in an adhesive patch base containing 5 to 90 wt % of a styrene-isoprene-styrene block copolymer, 5 to 70 wt % of a hydrogenated rosin glycerin ester, 10 to 70 wt % of liquid paraffin, and 1 to 10 wt % of an absorption promoter, wherein a blend ratio between the hydrogenated rosin glycerin ester and donepezil is hydrogenated rosin glycerin ester/donepezil=1.5 to 8, and a blend ratio between the styrene-isoprene-styrene block copolymer and liquid paraffin is styrene-isoprene-styrene block copolymer/liquid paraffin=0.7 to 1.5.

* * * * *